United States Patent [19]

Estes

[11] Patent Number: 5,578,034
[45] Date of Patent: Nov. 26, 1996

[54] APPARATUS FOR PREVENTING SCREW BACKOUT IN A BONE PLATE FIXATION SYSTEM

[75] Inventor: Bradley T. Estes, Memphis, Tenn.

[73] Assignee: Danek Medical, Inc., Memphis, Tenn.

[21] Appl. No.: 477,296

[22] Filed: Jun. 7, 1995

[51] Int. Cl.$^6$ .................................................. A61B 17/80
[52] U.S. Cl. .................. 606/61; 606/69; 606/73; 606/78; 411/909
[58] Field of Search ............................... 606/73, 60, 61, 606/66, 69, 70, 71, 72, 78; 411/909, 533, 970, 999, 352, 353

[56] References Cited

U.S. PATENT DOCUMENTS

| 4,484,570 | 11/1984 | Sutter et al. | 128/92 |
|---|---|---|---|
| 4,880,343 | 11/1989 | Matsumoto | 411/222 |
| 5,261,909 | 11/1993 | Sutterlin et al. | 606/61 |
| 5,269,784 | 12/1993 | Mast | 606/69 |
| 5,275,601 | 1/1994 | Gogolewski et al. | 606/72 |
| 5,290,289 | 3/1994 | Sanders et al. | |
| 5,364,399 | 11/1994 | Lowery et al. | 606/69 |
| 5,366,331 | 11/1994 | Erbes | 411/433 |

OTHER PUBLICATIONS

George B. Kauffman, *The Metal With a Memory*, Invention & Technology, 1993, pp. 18–23.

*Primary Examiner*—Guy V. Tucker
*Assistant Examiner*—David O. Reip
*Attorney, Agent, or Firm*—Woodard, Emhardt, Naughton, Moriarty & McNett

[57] ABSTRACT

A system for internal fixation of bone includes a fixation plate having a number of bores therethrough, a corresponding number of screws each having an enlarged head portion and an elongated shaft portion defining bone engaging threads thereabout and a non-threaded portion between the head and threaded portions, and a corresponding number of screw anti-backout members each having a bore therethrough. The screw anti-backout members are positioned within the bores of the fixation plate and are initially sized to slidingly receive an elongated shaft therethrough. The screws are advanced through the plate bores and screw anti-backout members so that the fixation plate is secured to the underlying bone with the bores of the screw anti-backout members surrounding a non-threaded portion of the shafts. The system is thereafter heated sufficiently to shrink the bores of the screw anti-backout members, thereby trapping the non-threaded portions of the screw shafts between the fixation plate and the threaded portions.

25 Claims, 6 Drawing Sheets

APPARATUS FOR PREVENTING SCREW BACKOUT IN A BONE PLATE FIXATION SYSTEM

FIELD OF THE INVENTION

The present invention relates generally to systems for securing a fixation plate to bone, and more specifically to such systems including a mechanism for preventing screw backout.

BACKGROUND OF THE INVENTION

Within the last decade, the use of fixation plates for the treatment of spinal disorders or for fusion of vertebrae has grown considerably. While early procedures using fixation plates were generally restricted to long bones and lower lumbar levels of the spine, such fixation plates have recently found applications in other bone instrumentation such as in instrumentation of the cervical spine. Successful spinal instrumentation in this region is particularly difficult given the problems of safely accessing the instrumentation site.

One typical example of a bone fixation plate is provided with a plurality of bores therethrough. A corresponding plurality of fastener members, typically bone screws having a headed portion and an elongated threaded shaft extending therefrom, are provided to secure the plate to a bone, or bones, to be fixated. The bone screws are advanced into the corresponding plate bores and then into the bone itself. The screws are then firmly tightened to thereby secure the plate to the bone.

A common problem associated with the use of such fixation plates, regardless of their location, is the tendency of the bone screws to "back out" of the underlying bone under the stress of bodily movement. This problem is particularly prevalent in areas of high stress such as, for example, the spine. Given the delicate nature of the spine, any fixation plate movement post-operatively may not only frustrate the surgical goals, but may also raise genuine patient safety concerns.

Designers of such bone fixation systems have employed various techniques in an attempt to overcome the foregoing problem. For example, U.S. Pat. No. 5,364,399 to Lowery et al., assigned to the assignee of the present invention, discloses an anterior cervical plating system incorporating a locking screw which engages the heads of bone screws to secure the cervical plate to the vertebra. The locking screw, positioned above the bone screws, provides a rigid fixation of the screws to the plate wherein the heads of the bone screws are either flush with, or recessed below, the upper surface of the plate.

As another example, U.S. Pat. No. 5,275,601 to Gogolewski et al. discloses a self-locking bone fixation system wherein the heads of the bone screws are frustoconical in shape and have a directionally corrugated outer surface. Each bore in the fixation plate has a complementarily corrugated inner surface and is similarly frusto-conical in shape. As the screws are advanced through the corrugated bores and into the underlying bone, the direction of corrugation permits the heads to be received within the corresponding bores, while inhibiting rotation of the screws in an opposite direction.

As a further example, U.S. Pat. No. 5,269,784 to Mast discloses a threaded screw nut for use with a bone fixation system wherein the screw nut is partially insertable into a bore of the fixation plate from the underside thereof, and threadingly engages a portion of the bone screw to thereby secure the bone screw to the fixation plate.

As a final example, U.S. Pat. No. 4,484,570 to Sutter et al. discloses a bone fixation system wherein the heads of the bone screws are hollow and expandable. After the fixation plate is secured to the underlying bone via the hollow head bone screws, set screws are advanced into the hollow heads to expand the heads and thereby secure the heads to the fixation plates.

All of the foregoing prior art systems suffer from several undesirable drawbacks. First, the addition of intricately machined componentry makes most of these systems expensive and difficult to manufacture. Second, since some of these prior art systems rely on a threaded connection to maintain the bone screws in a secure position, such locking systems are still subject to the problem of screw back out and may therefore be unreliable. Finally, most of the foregoing systems, by their nature, result in an increased profile or bulk which, in many surgical applications, is undesirable. What is therefore needed is a bone fixation system including a mechanism for preventing screw backout without increasing the profile or bulk of the fixation system. Such a system should ideally be easy and inexpensive to manufacture.

SUMMARY OF THE INVENTION

The bone fixation plate system of the present invention addresses and overcomes the foregoing drawbacks of prior art systems. In accordance with one aspect of the present invention, a bone fixation apparatus comprises a bone fixation plate having a bottom surface adapted to engage a portion of the bone being fixated, an opposite top surface and a bore defined therethrough, a bone screw having an elongated shaft and an enlarged head portion engaging the bore at the top surface of the plate when the shaft extends therethrough, wherein the shaft defines a first diameter non-threaded portion adjacent the head portion and bone engaging threads remote from the head portion, and an annular locking collar substantially surrounding the non-threaded portion of the bone screw shaft. The collar has an initial inner diameter greater than the second diameter of the elongated shaft. The collar is formed of a material such that the inner diameter shrinks in response to a change in temperature thereof to a final diameter smaller than the second diameter to thereby trap the collar between the head portion and the second diameter bone engaging threads of the bone screw.

In accordance with another aspect of the present invention, an apparatus for preventing a fastener from backing out of a fixation member bore is provided in combination with a fixation system including a fixation member having a top surface, a bottom surface and a bore defined therethrough, and a fastener having an elongated shaft and a headed portion engaging the bore at the top surface of the fixation member when the shaft extends therethrough. The apparatus comprises an annular collar having an initial inner diameter deformably sizable to slidingly receive the elongated shaft therethrough. The collar is formed of a material such that the inner collar diameter shrinks to a final diameter in response to a change in temperature thereof to thereby prevent the fastener from backing out of the fixation member bore. The collar further has an outer diameter sized to engage the bottom surface of the fixation member.

In accordance with a further aspect of the present invention, a method for securing a fixation plate having a number of bores therethrough to a bone with a corresponding number of bone screws wherein each of the screws have a headed portion and an elongated shaft extending therefrom defining a first diameter non-threaded portion adjacent the head portion and a second larger diameter bone engaging threaded portion remote from the head portion, comprises the steps off (1) forming a number of annular collars constructed of a shape memory alloy to have a final inner diameter less than the second diameter while the crystal structure of said alloy is in the austenite phase, (2) cooling the collars sufficiently so that the crystal structure of the alloy shifts to the martensite phase, (3) increasing the inner diameter of each of the annular collars while maintaining the collars in the martensite phase to permit passage therethrough of an elongated bone screw shaft, (4) mounting the fixation plate to the bone by advancing each of the number of bone screws through a corresponding fixation plate bore, through one of the annular collars and into the bone, and (5) heating the number of collars sufficiently to cause the inner diameters of the collars to shrink to their final diameters thereby trapping the number of Collars between the head portions and the threaded portions of the corresponding number of bone screws.

It is one object of the present invention to provide an apparatus for preventing screw backout, in a bone plate fixation system having a shape memory alloy collar for trapping a portion of the screw therein to thereby inhibit passage of the screw through the collar post-operatively.

It is another object of the present invention to provide a method of securing a fixation plate to a bone using a plurality of shape memory alloy collars surrounding a corresponding plurality of bone screws advanced through the fixation plate.

It is yet another object of the present invention to provide a system for preventing a bone screw from backing out of a bone fixation plate through the use of a shape memory alloy collar, wherein the profile of the system is not increased by using the collar.

These and other objects of the present invention will become more apparent from the following description of the preferred embodiment.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
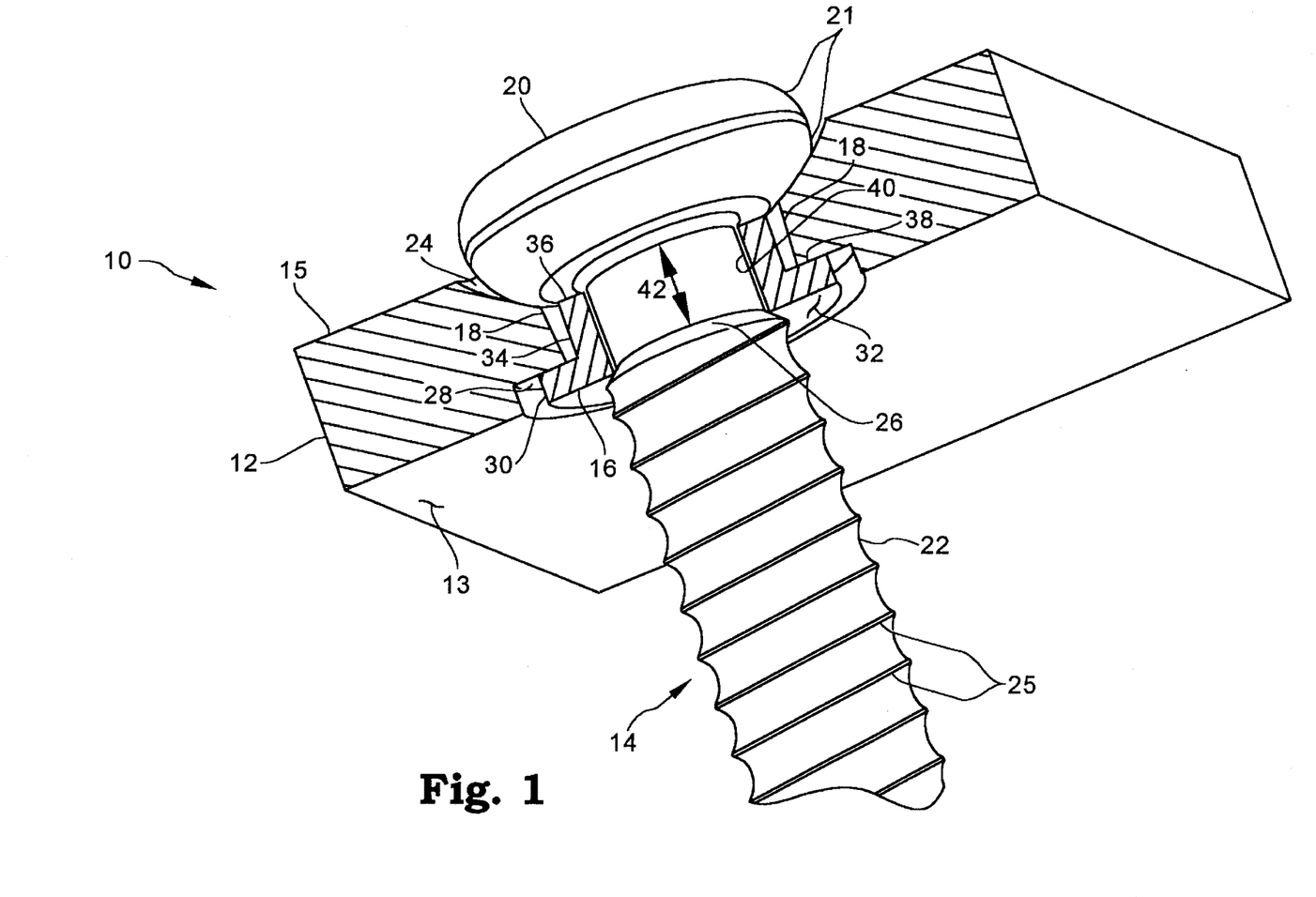
FIG. 1 is a perspective and partial cross sectional view of one embodiment of a fixation plate and screw anti-backout system in accordance with the present invention.

Referring now to FIG. 1, one embodiment of a fixation plate and screw anti-backout system 10, in accordance with the present invention, is shown. Fixation plate 12 has a bore 18 therethrough which is sized to slidingly receive a fastening element therein to thereby secure the fixation plate to its intended surface. Preferably, fixation plate 12 is a spinal fixation plate, although the present invention contemplates that fixation plate 12 may include any type of fixation plate used to reinforce a bone, join two, or more bones, or provide an anchoring location at a specified bone location.

System 10 further includes a fastening element 14 having an enlarged headed portion 20 and an elongated shaft portion 22 extending therefrom. The elongated shaft 22 of fastening element 14 is slidingly received within bore 18 of fixation plate 12 such that the enlarged headed portion 20 rests against the top portion 24 of bore 18 adjacent the top surface 15 of fixation plate 12. Enlarged head portion 20 of fastening element 14 is sized large enough so that it cannot pass through the smaller sized bore 18, and is preferably configured so that it seats within the top portion 24 of bore 18. As shown in FIG. 1, top portion 24 of bore 18 is preferably recessed from top surface 15 of fixation plate 12 in a semi-circular shape to facilitate the seating of head portion 20 of fastening element 14 therein.

Preferably, fastening element 14 is a bone screw having bone engaging threads 25 defined along at least a portion of elongated shaft 22. Bone screw 14 further has a cylindrically-shaped head 20 with rounded edges 21. Preferably, rounded edges 21 and top portion 24 of bore 18 are complementarily configured to facilitate seating contact therebetween. Although fastening element 14 is, in a preferred embodiment, a bone screw as shown in FIG. 1, the present invention contemplates the use of other bone engaging screw embodiments for use in securing fixation plate 12 to bone.

Figure 3A:
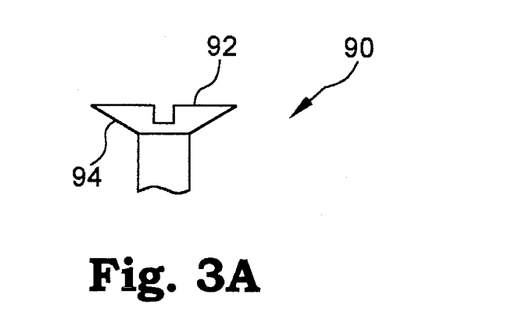
FIG. 3A is a front elevational view of one embodiment of the head portion of a fastener for use with a fixation plate and screw anti-backout system of the present invention.
Figure 3B:
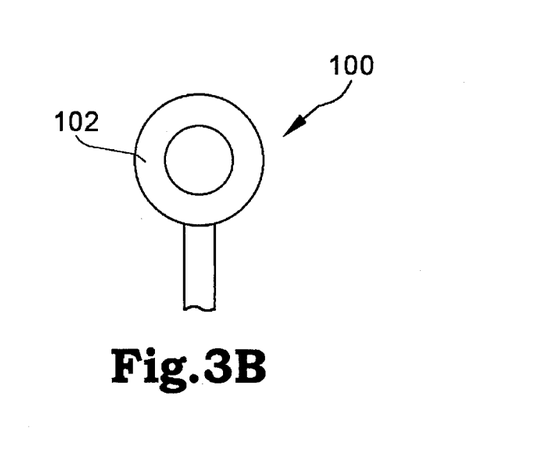
FIG. 3B is a front elevational view of another embodiment of the head portion of a fastener for use with a fixation plate and screw anti-backout system of the present invention.
Figure 3C:
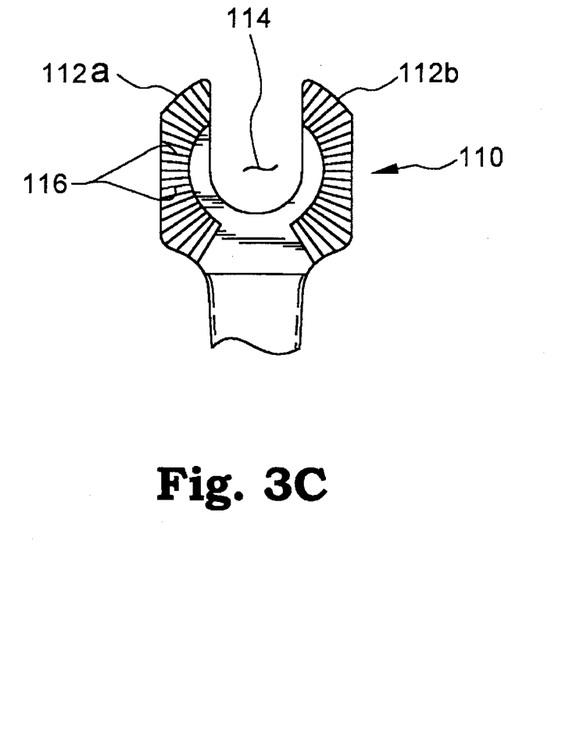
FIG. 3C is a front elevational view of a further embodiment of the head portion of a fastener for use with a fixation plate and screw anti-backout system of the present invention.

For example, referring to FIG. 3A, the headed portion 20 of fastening element 14 may be configured as a flat head screw 90 having a substantially flat top surface 92 and frusto-conically shaped sidewalls 94. With such a configuration, top portion 24 of bore 18 should be similarly frusto-conically shaped so that the headed portion 60 can be counter sunk therein with top surface 92 thereafter being flush with top surface 15 of fixation plate 12. Referring now to FIG. 3B, headed portion 20 of fastening element 14 may further be configured as an eye-bolt head 100 having a substantially circular ring 102. Finally, referring to FIG. 3C, headed portion 20 of fastening element 14 may further be configured as a headed portion 110 of a variable angle screw. Headed portion 110 of the variable-angle screw includes a pair of sides 112*a* and 112*b* which form a U-shaped passage 114 therebetween. One side of head portion 110 defines a series of radially extending teeth or splines 116 which are formed to interdigitate with splines on a corresponding component (not shown). An example of such a variable angle screw is disclosed in U.S. Pat. No. 5,261,909 to Sutterlin et al., the contents which are incorporated herein by reference.

Figure 4A:
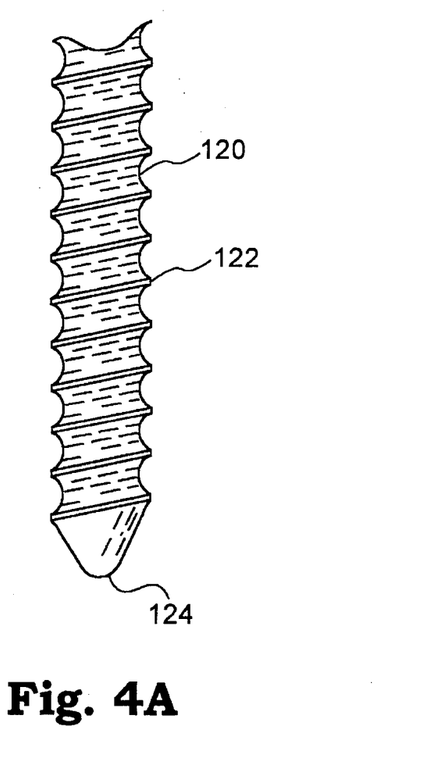
FIG. 4A is a front elevational view of one embodiment of the shaft portion of a fastener for use with a fixation plate and screw anti-backout system of the present invention.
Figure 4B:
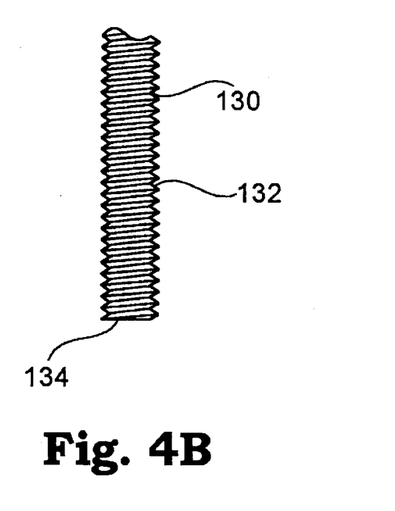
FIG. 4B is a front elevational view of an alternate embodiment of the shaft portion of a fastener for use with a fixation plate and screw anti-backout system of the present invention.
Figure 4C:
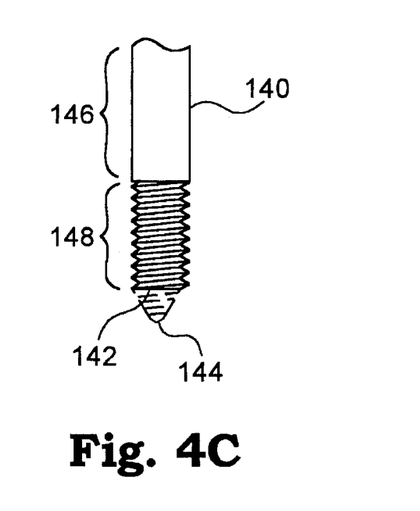
FIG. 4C is a front elevational view of another alternate embodiment of the shaft portion of a fastener for use with a fixation plate and screw anti-backout system of the present invention.

Referring again to FIG. 1, a portion of elongated shaft 22 of fastening element 14 preferably includes bone-engaging threads 25. An example of one such elongated shaft 120 is shown in FIG. 4A. Shaft 120 includes bone-engaging threads 122, and terminates in a pointed (self-tapping) end 124. An example of another elongated shaft 130 is shown in FIG. 4B. Shaft 130 includes threads 132, and terminates in a flat end 134. Finally, a further embodiment of elongated shaft 140 is shown in FIG. 4C. Shaft 140 may terminate in a flat end 142, or may have a pointed (self-tapping) end 144 as shown in phantom. A portion 146 of elongated shaft 140, between head portion (not shown) and end portion 142 or 144, is not threaded. Threaded portion 148 is included below non-threaded portion 146 and is remote from the head portion (not shown). Although the elongated shaft embodiments shown in FIGS. 4A–4C are preferably used in a bone fixation system, any of the threaded shaft embodiments shown therein may be provided with any number of threads per inch (TPI) to meet a desired bone engaging need.

Referring again to FIG. 1, regardless of the type of fastening element 14 used, elongated shaft 22 preferably includes a reduced diameter non-threaded portion 42 between head portion 20 and the threaded portion 25 of shaft 22. Although shaft portion 22 need not have a reduced diameter portion 42 to be operable in system 10, the diameter of portion 42 is reduced in a preferred embodiment to optimize the screw anti-backout feature as will be more fully described hereinafter.

Figure 2:
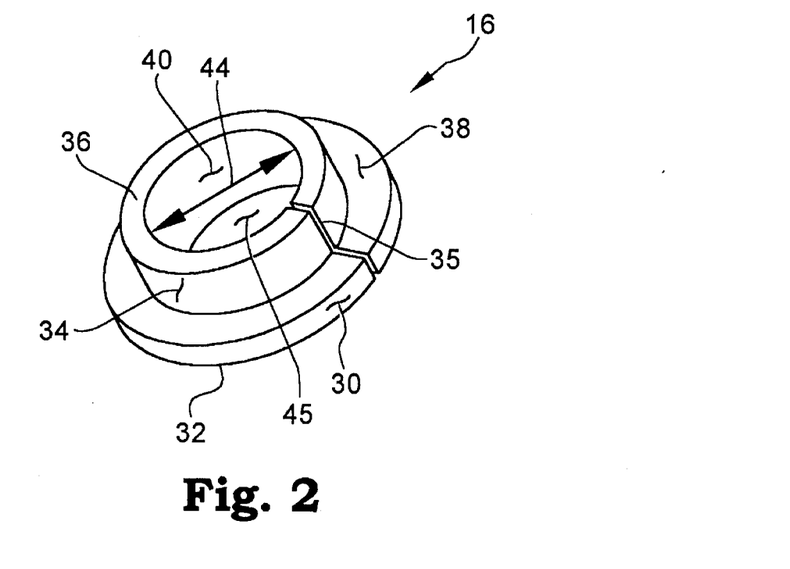
FIG. 2 is a perspective view of the screw anti-backout member shown in FIG. 1.

Referring now to FIGS. 1 and 2, system 10 further includes an annular ring 16 having a bore 45 therethrough defining an inner annular surface 40 having a diameter 44. Collar 16 further has an outer annular surface 34. Inner and outer annular surfaces 40 and 34, respectively, terminate at a top end 36 and an opposite bottom end 32. A flange 30 extends radially from outer surface 34 adjacent bottom end 32 and has a top surface 38 for engaging a portion of fixation plate 12. A channel 35 extends between bottom end 32 and top end 36 of collar 16, and extends from flange 30 and outer surface 34 into bore 45. Preferably, collar 16 is of unitary construction and is formed of a material that is responsive to a change in temperature to assume either an expanded or a retracted shape.

One example of a material that is responsive to a change in temperature to assume a retracted shape is a shape memory alloy. In order for an alloy to exhibit a shape memory effect, it must be a crystalline structure which can change its structure into the so-called austenite phase when it is subjected to a certain temperature condition, and then change its structure into the so-called martensite phase when the temperature of the alloy is sufficiently lowered. In providing a shape memory alloy component, the component is first annealed to a specified shape by traditional means. The alloy is then heated to a temperature high enough that the crystalline structure assumes the austenite phase or configuration. Next, the alloy is cooled until it reverts to the martensite phase or configuration. Once in the martensite configuration, the component may be further deformed randomly, but will return to its original austenite phase shape when heated to a temperature above that at which the martensite phase returns to the austenite phase. Thus, after being deformed in the martensite phase, the alloy "remembers" its original annealed shape and will return to that original shape when heated above the austenite phase transition temperature. In so doing, the alloy converts heat energy into mechanical work. The mechanical work done while the material is undergoing shape recovery can be much greater than originally imparted during the initial plastic deformation.

The shape memory alloy of collar 16 is preferably made of a nickel-titanium alloy such as nitinol. The specific transitional temperature at which the phase transition occurs can be controlled by specifying the exact nickel to titanium ratio. In a preferred embodiment of annular collar 16, the nickel-titanium ratio is chosen to provide an austenite transition temperature of approximately 42° C. and a martensite transition temperature of approximately 10° C. However, the present invention contemplates other nickel-titanium ratios to provide desired austenite and martensite phase transition temperatures. It is to be understood that different applications of fixation plate and screw anti-backout systems described herein will require different phase transition temperatures, and that the present invention contemplates any nickel-titanium ratio required to meet such specific applications. The present invention further contemplates the use of other known shape memory alloys for use in constructing annular collar 16. An example of one such alloy is an iron-based alloy including various percentages by weight of manganese, silicon, and chromium.

According to a preferred approach in constructing annular collar 16, collar 16 is first deformed while in the austenite phase crystalline configuration such that inner annular surface 40 has a diameter 44 less than the diameter of reduced diameter portion 42 of fastener element 14. Collar 16 is then cooled until the martensite transformation occurs. While maintaining collar 16 below the shape transition temperature, collar 16 may be deformed to increase the inner diameter thereof.

Figure 5A:
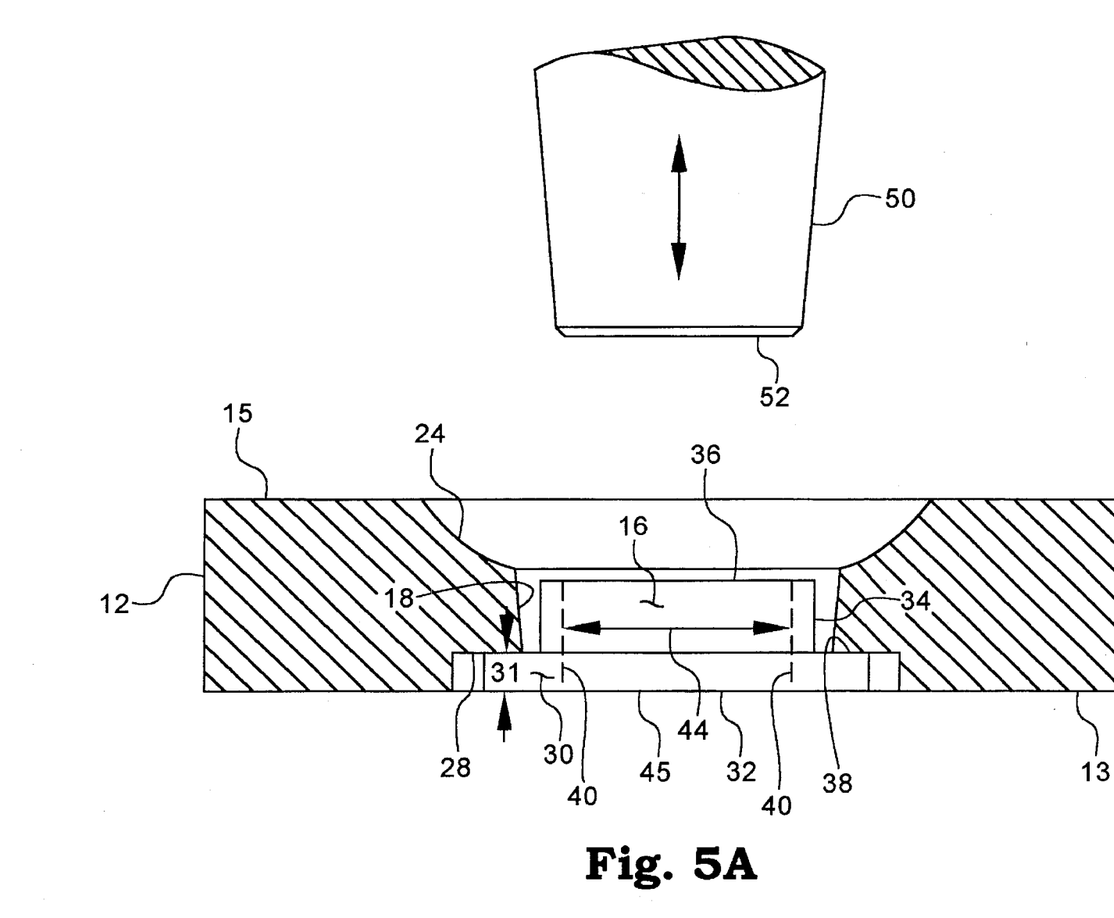
FIG. 5A is a side elevational and partial cross sectional view of the fixation plate and screw anti-backout member assembly of FIG. 1, showing the use of a tapered instrument to increase the inner diameter of the screw anti-backout member.

Referring now to FIG. 5A, bore 18 of fixation plate 12 is sized to slidingly receive the outer surface 34 of collar 16 therein such that the top portion 36 of collar 16 is adjacent top portion 24 of bore 18. Preferably, although not necessarily, fixation plate 12 includes a recess 28 about bore 18 having a depth approximately equal to the thickness 31 of flange 30. Advantageously, recess 28 permits the bottom portion 32 of collar 16 to be flush with the bottom portion 13 of fixation plate 12 so that the vertical profile of fixation plate locking system 10 is not increased due to the use of collar 16. A taper instrument 50 is provided to "open up" collar 16 for passage therethrough of the elongated shaft 22 of fastening element 14. Taper instrument 50 has a first end 52 which has a diameter slightly less than inner diameter 44 of collar 16. The diameter of taper instrument 50 increases at increasing distances from end 52.

As taper instrument 50 is advanced into the bore 45 of collar 16 from the top 36 thereof, channel 35 is widened, thereby deforming, or spreading open, collar 16 to an initial inner diameter such that the outer surface 34 of collar 16 is forced against the walls of bore 18. To facilitate the advancement of taper instrument 50 into collar 16 to thereby sufficiently spread open the inner surface 40 of collar 16, the walls of bore 18 may be tapered complementary to the taper of instrument 50. The decreasing diameter of bore 18 in a direction toward the bottom 13 of plate 12 further acts to retain collar 16 within bore 18 when taper instrument 50 is removed therefrom. In this way, collar 16 may be pre-loaded into bore 18 prior to positioning plate 12 within a patient.

With collar 16 so deformed in the martensite phase to have an initial inner diameter greater than diameter 44, elongated shaft 22 of fastening element 14 may be slidably received therethrough. Fastener 14 is then advanced through bore 45 and into the bone to be fixated. As fastening element 14 is sufficiently advanced, headed portion 20 is secured against top portion 24 of bore 18, and collar 16 surrounds reduced diameter portion 42 of fastening element 14. In this position, fixation plate 12 should be rigidly secured to the underlying structure to be fixated.

After securing fixation plate 12 to the underlying bone to be fixated, collar 16 is heated sufficiently to transform the alloy to the austenite phase configuration. In so doing, collar 16 "remembers" its original configuration, and its inner diameter 44 shrinks in size. The heating step may take the form of simply allowing the collar to warm to body temperature, or may involve other known methods such as inducing electrical currents in collar 16 through the use of electromagnetic waves, or through the use of a sufficiently warm fluid such as water or saline.

Since the original diameter 44 was less than the diameter of reduced diameter portion 42 of fastening element 14, the inner surface 40 of collar 16 "grips" reduced diameter portion 42 to thereby rigidly clamp fastening element. In this clamping arrangement embodiment, top surface 38 of flange 30 abuts recess 28 of fixation plate 12, and the bottom portion 32 of flange 30 abuts transition surface 26 located between reduced diameter portion 42 and threaded portion 25 of fastening element 14.

Figure 5B:
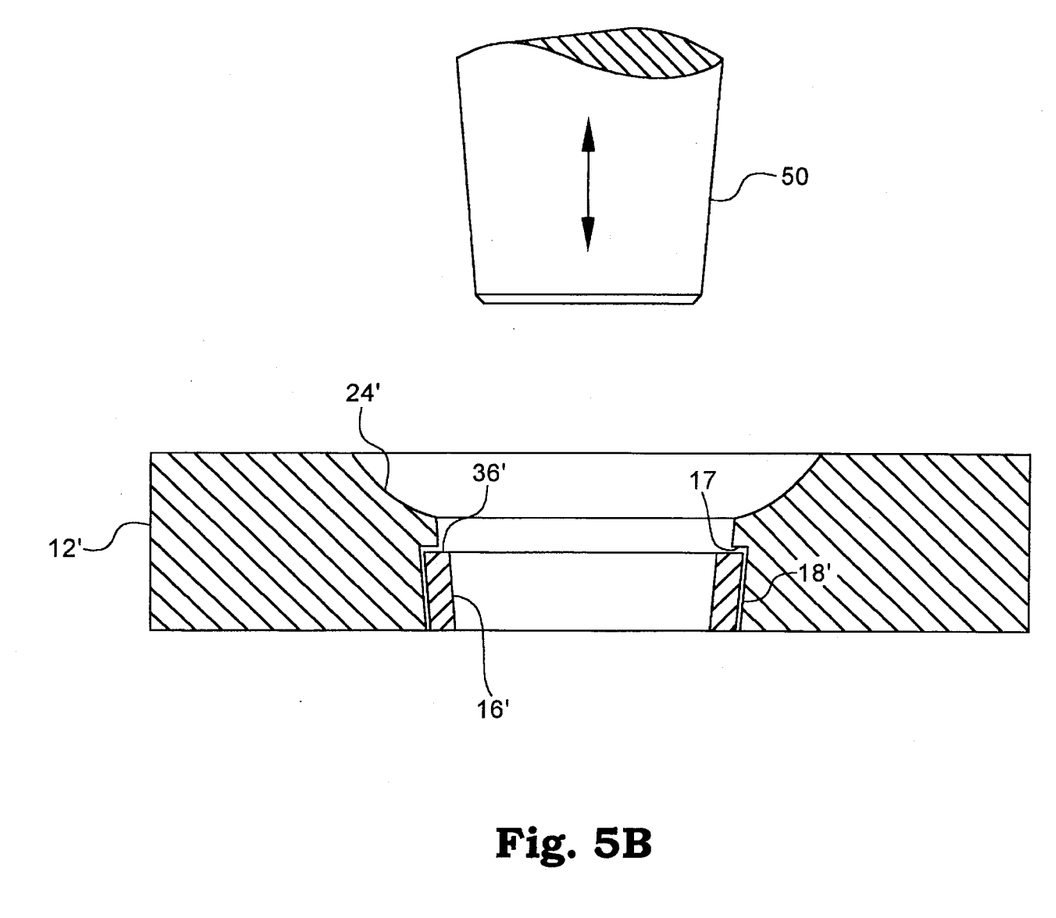
FIG. 5B is a cross-sectional view of an alternate embodiment of a fixation plate and screw anti-backout system in accordance with the present invention, including the use of a tapered instrument to increase the inner diameter of the screw anti-backout member.

Flange 30 of collar 16 thus provides a positive stop for collar 16 in the direction of top portion 24 of bore 18. Referring to FIG. 5B, this feature may alternatively be provided by configuring the inner surface of bore 18' with a step 17 adjacent top portion 24' to thereby abut top 36' of collar 16'. With such a configuration, flange 30 is not necessary and collar 16' need only be provided with sufficient thickness so that its outer diameter will not slip past the step 17 when undergoing an austenite phase transformation. Collar 16' is shown in FIG. 5B as assuming a characteristic position against bore 18' of fixation plate 12' after insertion and withdrawal of tapered instrument 50.

The reduced diameter portion 42 of fastening element 14 optimizes fixation plate clamping system 10 by ensuring that locking clamp 16, once reduced in diameter, will not slip toward threads 25. However, the present invention contemplates that the gripping force of locking clamp 16, in many applications, will provide sufficient clamping force so that fastening element 14 need not include a reduced diameter portion 42 and transition surface 26. Regardless of its diameter, portion 42 of shaft 22 should be non-threaded to maximize the surface area between portion 42 and the inner surface 40 of collar 16, although portion 42 may, in some applications, be threaded if the threads are sufficiently shallow and/or the TPI is high enough to permit collar 16 to grip portion 42 with sufficient strength.

According to an alternate approach in utilizing shape memory collar 16, the initial diameter 45 thereof may be deformed while in the austenite phase crystalline configuration such that the inner annular surface 40 has a diameter 44 slightly larger than reduced diameter portion 42 of fastening element 14, but less than the diameter of threaded portion 25. With such an approach, the reduced diameter collar need not "grip" reduced diameter portion 42 in its final configuration. Rather, the inner diameter 44 of collar 16 need only shrink enough to disallow threaded portion 25 to advance therethrough. Collar 16, although loosely surrounding reduced diameter portion 42 of fastening element 14, prevents fastening element 14 from backing out of bore 18 by having a final inner diameter less than that necessary to permit threaded portion 25 to pass therethrough.

In any event, the now reduced diameter collar 16 prevents fastening element 14 from backing out of the surface in which it has been advanced. It is to be understood that a typical fixation plate, regardless of its area of application, will likely have multiple bores 18 and fastening elements 14 and, as such, the present invention contemplates providing a locking collar 16 for each fastening element 14 and bore 18 pair.

Figure 6:
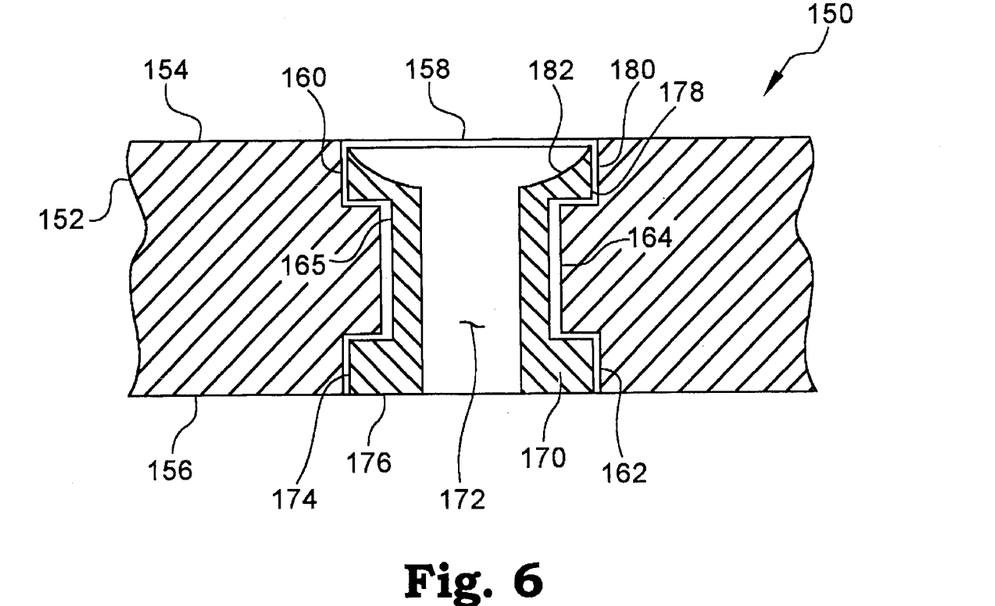
FIG. 6 is a cross-sectional view of another alternate embodiment of a fixation plate and screw anti-backout system in accordance with the present invention.

Referring now to FIG. 6, another embodiment of a fixation plate and screw anti-backout system 150, in accordance with the present invention, is shown. System 150 includes a fixation plate 152 having a top surface 154 and an opposite bottom surface 156. Fixation plate 152 includes a number of bores 158 therethrough, each for receiving an elongated shaft 22 of a fastening element 14 therein as previously discussed with respect to FIG. 1. A substantial portion of bore 158 has a first diameter 164. In its bottom surface 156, plate 152 defines a recess 162 about bore 158. In its top surface 154, plate 152 defines another recess 160 about bore 158. Each of recesses 160 and 162 intersect bore 158 and have diameters larger than bore diameter 164.

An annular collar 170, identical in function to collar 16, is positioned within bore 158. Collar 170 defines a variable diameter bore 172 therethrough identical in operation to bore 18 of collar 16. Collar 170 further has a first flange 174 extending radially away from collar outer surface 165 adjacent the bottom 176 thereof, and a second flange 178 extending radially away from outer surface 165 adjacent the top 180 thereof. The top surface 182 of bore 172 is recessed, similar to top surface 24 of bore 18 described with respect to FIG. 1, to facilitate the seating of head portion 20 of fastening element 14 therein. Although not shown in FIG. 6, collar 170 further includes a longitudinal channel therethrough similar to channel 35 of collar 16.

Operationally, collar 170 may be pre-loaded into bore 158 by pinching the outer surface 165 thereof with suitable means so that the channel (not shown) width decreases. As a result, the outer diameter of collar 170 may be made to shrink sufficiently to permit either of flanges 174 or 178 to pass through the first diameter 164 portion of bore 158. Collar 170 may thus be top-loaded (from top surface 154 of plate 152) or bottom-loaded (from bottom surface 156 of plate 152) into bore 158 such that flanges 176 and 178 cooperate with recesses 162 and 160 respectively to maintain collar 170 in position within bore 158 as shown in FIG. 6.

Figure 7:
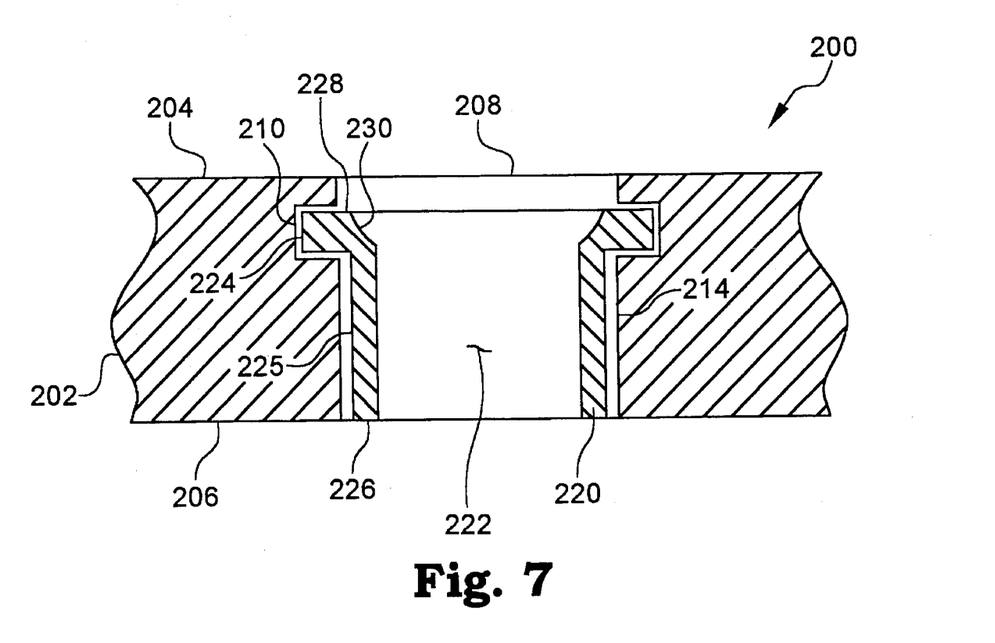
FIG. 7 is a cross-sectional view of still another alternate embodiment of a fixation plate and screw anti-backout system in accordance with the present invention.

Referring now to FIG. 7, yet another embodiment of a fixation plate and screw anti-backout system 200, in accordance with the present invention, is shown. System 200 includes a fixation plate 202 having a top surface 204 and an opposite bottom surface 206. Fixation plate 202 includes a number of bores 208 therethrough, each for receiving an elongated shaft 22 of a fastening element 14 therein as previously discussed with respect to FIG. 1. A substantial portion of bore 208 has a first diameter 214. Bore 208 defines an annular recess 210 therein which is sized slightly larger than bore diameter 214. Preferably, annular recess 210 is located near top surface 204 of plate 202, although the present invention contemplates that annular recess 210 may be located anywhere within bore 208.

An annular collar 220, identical in function to collars 16 and 170, is positioned within bore 208. Collar 220 defines a variable diameter bore 222 therethrough identical in operation to bore 18 of collar 16 (and bore 172 of collar 170). Collar 220 further has a flange 224 extending radially away from collar outer surface 225 adjacent the top 228 thereof. The top surface 230 of bore 222 is recessed, similar to top surface 24 of bore 18 described with respect to FIG. 1, to facilitate the seating of head portion 20 of fastening element 14 therein. As with collar 170, collar 220 further includes a longitudinal channelotherethrough (not shown) similar to channel 35 of collar 16.

Operationally, collar 220 may be pre-loaded into bore 208 by pinching the outer surface 225 thereof with suitable means so that the channel (not shown) width decreases. As a result, the outer diameter of collar 220 may be made to shrink sufficiently to permit flange 224 to pass through the first diameter 214 portion of bore 208. Collar 220 may thus be top-loaded (from top surface 204 of plate 202) or bottom-loaded (from bottom surface 206 of plate 202) into bore 208 such that flange 224 cooperates with recesses 210 to maintain collar 220 in position within bore 208 as shown in FIG. 7. Preferably, collar 220 is positioned within bore 208 such that the bottom 226 of collar 220 is flush with the bottom surface 206 of plate 202.

In function and operation, collars 170 and 220 are identical to collar 16. As illustrated in FIGS. 6 and 7, however, the present invention contemplates that the screw anti-backout collar 16, 16', 170 and 220) may be variously configured to facilitate the retention of the collar within the corresponding fixation plate bore prior to positioning and securing the plate within a patient. Those skilled in the art will recognize that other such collar and fixation plate bore configurations may be designed to provide this feature, it being understood that such alternate configurations are contemplated by the present invention and therefore fall within the spirit of the Concepts described herein.

Any of collars 16, 16', 170 and 220 may further be formed of a material that is responsive to a change in temperature to expand in thickness, such as in response to heat. Thus, in response to an increase in temperature, the collar inner diameter "shrinks" due to expansion of the collar thickness. Advantageously, the outer diameter correspondingly grows so as to decrease any play between the bore of the fixation plate and the outer surface of the collar. Such a heat expandable material may include, for example, an epoxy, elastomer or other "curable" material, or any of a variety of heat-expandable rigid materials.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A bone fixation apparatus comprising:

a bone fixation plate having a bottom surface adapted to engage a portion of the bone being fixated, an opposite top surface and a bore defined therethrough;

a bone screw having an elongated shaft and an enlarged head portion engaging said bore at said top surface of said plate when said shaft extends therethrough, said shaft defining a first diameter non-threaded portion adjacent said head portion and bone engaging threads having a second larger diameter remote from said head portion; and an annular collar substantially surrounding said non-threaded portion of said bone screw shaft, said collar having an initial inner diameter greater than said second diameter, said collar being formed of a material such that said inner diameter shrinks in response to a change in temperature thereof to a final diameter smaller than said second diameter to thereby trap said collar between said head portion and said second diameter bone engaging threads of said bone screw.

2. The bone fixation apparatus of claim 1 wherein said collar material is a shape memory alloy.

3. The bone fixation apparatus of claim 2 wherein said inner diameter of said annular collar further shrinks in response to said change in temperature to a final diameter less than said first diameter to thereby rigidly clamp said non-threaded portion.

4. The bone fixation apparatus of claim 2 wherein said shape memory alloy is a nickel-titanium alloy.

5. The bone fixation apparatus of claim 2 wherein said annular collar transforms from a martensite phase to an austenite phase as the temperature thereof is increased above a phase transformation temperature.

6. The bone fixation apparatus of claim 5 wherein the bone being fixated includes a portion of the spine.

7. The bone fixation apparatus of claim 1 wherein said annular collar has an outer surface opposite said inner diameter, said outer surface of said collar having a first flange extending radially therefrom, said collar thereby trapping said fixation plate between said head portion and said flange.

8. The bone fixation apparatus of claim 7 wherein said fixation plate bore defines a longitudinal axis from said top surface of said plate to said bottom surface of said plate;

and wherein said first flange contacts said bottom surface of said plate to thereby inhibit movement of said collar along said longitudinal axis in a direction toward said top surface of said plate.

9. The bone fixation apparatus of claim 8 wherein said collar has a top end and an opposite bottom end, said first flange extending radially away from said outer surface thereof adjacent said bottom end thereof;

and wherein said bore of said fixation plate is configured to receive said outer surface of said collar therein such that said first flange abuts said bottom surface of said fixation plate.

10. The bone fixation apparatus of claim 9 wherein said first flange has an inner flange surface and an opposite outer flange surface;

and wherein said bottom surface of said fixation plate defines a first recess therein around said fixation plate bore, said first recess being adapted to receive said first flange therein such that said outer surface of said first flange is flush with said bottom surface of said fixation plate.

11. The bone fixation apparatus of claim 9 wherein said outer surface of said collar has a second flange extending radially therefrom;

and wherein said second flange contacts said top surface of said plate to thereby inhibit movement of said collar along said longitudinal axis in a direction toward said bottom surface of said plate.

12. The bone fixation apparatus of claim 11 wherein said second flange has an inner flange surface and an opposite outer flange surface;

and wherein said top surface of said fixation plate defines a second recess therein around said fixation plate bore, said second recess being adapted to receive said second flange therein such that said outer surface of said second flange is recessed below said top surface of said fixation plate.

13. The bone fixation apparatus of claim 7 wherein said fixation plate bore defines an annular recess therein, said annular recess receiving said first flange therein to thereby inhibit movement of said collar toward said top and bottom surfaces of said fixation plate.

14. The bone fixation apparatus of claim 1 wherein said collar has a top end and an opposite bottom end;

and wherein said fixation plate bore includes a stepped portion, said top end of said collar contacting said stepped portion of said fixation plate bore to thereby inhibit movement of said collar in a direction toward said top surface of said plate.

15. A fixation system for use with a fixation member having a top surface, a bottom surface and a bore defined therethrough, said fixation system comprising: a fastener having an elongated shaft, a headed portion engagable with the bore at the top surface of the fixation member when the shaft extends therethrough, a first diameter non-threaded portion adjacent said headed portion, and a second larger diameter threaded portion remote from said headed portion; and an apparatus for preventing the fastener from backing out of said bore when said shaft extends therethrough including an annular collar having an initial inner diameter deformably sizable to slidingly receive the elongated shaft therethrough and an outer diameter sized to engage said bottom surface of said fixation member, said collar being formed of a material such that said inner diameter shrinks to a final diameter less than the second diameter threaded portion of the fastener in response to a change in temperature thereof to thereby trap said fixation member between said collar and the headed portion of the fastener.

16. The fixation system of claim 15 wherein said final diameter of said collar is less than said first diameter non-threaded portion to thereby rigidly clamp said non-threaded portion of the fastener.

17. The fixation system of claim 15 wherein said collar material is a shape memory alloy.

18. The fixation system of claim 17 wherein said shape memory alloy is a nickel-titanium alloy.

19. The fixation system of claim 15 wherein said outer surface of said annular collar has a flange extending radially therefrom.

20. The fixation system of claim 19 wherein the fixation member defines a longitudinal axis from the top surface thereof to the bottom surface thereof;

and wherein said flange is adapted to contact the fixation member to hereby inhibit movement of the collar along the longitudinal axis in a direction toward the top surface of the, fixation member.

21. A method for securing a fixation plate having a number of bores therethrough to a bone with a corresponding number of bone screws wherein each of the screws have a headed portion and an elongated shaft extending therefrom defining a first diameter non-threaded portion adjacent the head portion and a second larger diameter bone engaging threaded portion remote from the head portion, the method comprising the steps of:

(1) forming a number of annular collars constructed of a shape memory alloy to have a final inner diameter less than the second diameter while the crystal structure of said alloy is in the austenite phase;

(2) cooling said collars sufficiently so that the crystal structure of said alloy shifts to the martensite phase;

(3) increasing the inner diameter of each of said annular collars while maintaining said collars in the martensite phase to permit passage therethrough of an elongated bone screw shaft;

(4) mounting the fixation plate to the bone by advancing each of the number of bone screws through a corresponding fixation plate bore, through one of said annular collars and into the bone; and (5) heating said number of collars sufficiently to cause said inner diameters of said collars to shrink to their final diameters thereby trapping the number of collars between the head. portions and the threaded portions of the corresponding number of bone screws.

22. The method of claim 21 wherein step (1) further includes forming said number of annular collars to have a final inner diameter less than the first diameter of the non-threaded portion of the bone screws.

23. The method of claim 21 wherein the heating of said number of collars is carried out by inducing electrical currents therein via electromagnetic waves.

24. The method of claim 21 wherein said shape memory alloy is a nickel-titanium alloy.

25. The method of claim 21 further including the step of providing each of said number of collars with a flange extending radially therefrom;

said collars trapping said fixation plate between collar flanges and the head portions of the corresponding bone screws.

\* \* \* \* \*